United States Patent [19]

Gednalski et al.

[11] Patent Number: 5,356,861
[45] Date of Patent: Oct. 18, 1994

[54] HOMOGENOUS HERBICIDAL ADJUVANT BLEND COMPRISING GLYPHOSATE, AMMONIUM SULFATE, AND ALKYL POLYSACCHARIDE

[75] Inventors: Joe V. Gednalski, Riverfalls, Wis.; Robert W. Herzfeld, Stillwater, Minn.

[73] Assignee: Cenex/Land O'Lakes Agronomy Company, St. Paul, Minn.

[21] Appl. No.: 154,970

[22] Filed: Nov. 19, 1993

[51] Int. Cl.⁵ .................. A01N 25/30; A01N 57/04
[52] U.S. Cl. .................. 504/206; 71/DIG. 1
[58] Field of Search ............ 504/206; 71/DIG. 1

[56] References Cited

U.S. PATENT DOCUMENTS 5,116,401  5/1992  Young .......................... 71/86

OTHER PUBLICATIONS

Grossbord et al. *The Merbicide Glyphosate*, p. 223–229, 1985.

Hoorne et al. "Novel Adjusvants for Agrodremical for Medations Based on Sugar Ethers", ICI Reprint RP67/91E. 1991.

*Primary Examiner*—Richard L. Raymond
*Assistant Examiner*—S. Mark Clardy
*Attorney, Agent, or Firm*—Kinney & Lange

[57] ABSTRACT

The present invention includes a homogenous blend for use with a herbicide comprising water, ammonium sulfate and alkyl polysaccharide, with a concentration of about 8.5 pounds of ammonium sulfate or about 2.5 gallons of the blend. The present invention also includes a method for making the homogeneous herbicidal blend, a method for killing broadleaf weeds.

2 Claims, No Drawings

HOMOGENOUS HERBICIDAL ADJUVANT BLEND COMPRISING GLYPHOSATE, AMMONIUM SULFATE, AND ALKYL POLYSACCHARIDE

BACKGROUND OF THE INVENTION

The present invention relates to a liquid homogenous adjuvant blend for use with a herbicide. The present invention also relates to a method for dissolving dry ammonium sulfate in water to form a homogenous adjuvant blend with a non-ionic surfactant.

While herbicides perform a useful function in killing undesirable plants in a particular location, herbicide use poses problems in the areas of uniform application, safety and aesthetics. Specifically, herbicides frequently have limited solubility in water, are hazardous to individuals applying the herbicides and emit an unpleasant odor.

Glyphosate, N-(phosphonomethyl)-glycine, has use as a broad spectrum, post emergence herbicide. When glyphosate is applied to selected weeds, the glyphosate translocates within the weeds as the weeds grow and kills the weeds. Glyphosate is typically applied to the weeds in conjunction with an ammonium sulfate fertilizer at a concentration of about 8.5 to 17 lbs. glyphosate and fertilizer per 100 gallons of an aqueous spray mixture. The combined exposure of weeds to the fertilizer and glyphosate can substantially increase the efficacy of the glyphosate. The fertilizer accelerates the translocation of the glyphosate herbicide within the weeds, increasing the kill rate of the weeds. The use of an inexpensive fertilizer can increase the efficacy of the glyphosate at a minimum cost.

Ammonium sulfate is an inexpensive fertilizer. However, use of ammonium sulfate is problematic because ammonium sulfate solubility in water varies with variable water qualities throughout the United States. Water temperatures, hardness and mineral content all effect ease of mixing of ammonium sulfate into the spray mixture. This unpredictable solubility has been problematic for individuals applying glyphosate to kill weeds in a crop. The individuals typically prepare mixtures that include glyphosate using cold water under conditions, frequently out-of-doors, where insolubility problems cannot be satisfactorily resolved. The individuals then face the prospect of trying to apply a messy suspension of ammonium sulfate in water with the glyphosate. The suspension plugs conveying lines, causes an uneven application of the suspension on a crop of weeds resulting in an uneven kill rate in a field and directly exposes an individual preparing the solution to undesirable herbicide and fertilizer contact.

These problems have been exacerbated by conventional packaging of the ammonium sulfate and the non-ionic surfactant. Presently, the non-ionic surfactant and ammonium sulfate are packaged separately. Ammonium sulfate is sold in bags of various sizes and the surfactant is sold in containers holding about 2.5 gallons. This conventional packaging poses problems in container disposal, especially when all of the ammonium sulfate and non-ionic surfactant are not used.

In addition to a fertilizer, an aqueous glyphosate application typically includes an addition of a non-ionic surfactant of about 0.5 to 2.0% volume/volume (v/v) for increased spreading and penetration of a leaf of a weed. Attempts have also been made to include a surfactant with the ammonium sulfate and water in order to improve the solubility or at least dispersibility of the glyphosate and ammonium sulfate in water of a wide quality range. Unfortunately, commonly used surfactants, including non-ionic surfactants such as nonoxynol have not been successful in either solubilizing or dispersing efficacious concentrations of ammonium sulfate in an aqueous solution also including glyphosate.

The Moller U.S. Pat. No. 5,118,338 issued Jun. 2, 1992, describes a solid composition that includes glyphosate and a surface-active agent such as a nonionic polyglycol ether of a fatty alcohol. The free acid of glyphosate is in a solid particulate state. The surface active agent is applied to the surface of the glyphosate particles and dries to a solid state.

The Girardeau et al. U.S. Pat. No. 4,867,972, issued Sep. 19, 1989, describes a wettable powder having at least one active material such as a herbicide and at least one surface-active agent including a copolymer of an unsaturated carboxylic acid or a derivative of the carboxylic acid. This mixture also includes a surface-active agent having the formula:

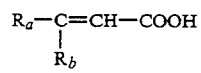

$R_b$ includes a compound with the formula:

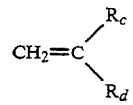

The composition also includes a surface-active agent that includes at least one mixed sulfate or phosphoric ester.

SUMMARY OF THE INVENTION

The present invention includes a homogeneous adjuvant blend for use with a herbicide having the components of water, ammonium sulfate, and alkyl polysaccharide in a concentration of about 8.5 pounds dry ammonium sulfate per 2.5 gallons of the homogeneous adjuvant blend.

The present invention also includes a method for making a homogeneous herbicidal blend that includes providing a quantity of water having a temperature of about 180° F., adding about 8.5 pounds of dry ammonium sulfate to about 1.5 gallons of the water to form a mixture, adding about 2.0 quarts of the alkyl polysaccharide and about 0.5 to 1.0 oz. of antifoam to the mixture of water and ammonium sulfate to form a homogeneous blend of about 2.5 gallons and mixing the homogeneous blend with a herbicide in water to a concentration of about 2.0 to 5.0% v/v to form a homogeneous herbicidal adjuvant blend.

DETAILED DESCRIPTION OF THE PREFERRED EMBODIMENTS

The present invention includes a liquid homogeneous adjuvant blend for use with a herbicide that includes the ingredients of water, ammonium sulfate, anti-foam and alkyl polysaccharide in a ratio of ammonium sulfate to the blend that is about 8.5 pounds of ammonium sulfate to 2.5 gallons of the blend. The present invention also includes a method for making a homogeneous herbicidal adjuvant blend that includes heating a quantity of water to a temperature of about 180° F., adding about 8.5 pounds of dry ammonium sulfate to about 1.5 gallons of the heated water, then adding about 2.0 quarts of alkyl polysaccharide to the water and ammonium sulfate, then adding 0.5 to 1.0 ounces of anti-foam and finally adding a herbicide and diluting to form a final homogeneous herbicidal adjuvant blend.

The homogeneous herbicidal blend of the present invention is a great improvement over herbicidal adjuvants in present use because the homogeneous blend of the present invention is a liquid having a concentration of ammonium sulfate and non-ionic surfactant that improves the effectiveness of herbicides such as glyphosate in killing weeds. Prior to the homogeneous blend of the present invention, ammonium sulfate could precipitate out of solution when other materials, such as glyphosate, were added to the solution. Thus, it was virtually impossible to prepare a homogeneous herbicidal blend of glyphosate having an effective concentration of ammonium sulfate. Consequently, neither the glyphosate nor the ammonium sulfate have been used very efficiently.

The homogeneous blend for use with a herbicide reduces the amount of time that herbicide applicators expend in mixing the glyphosate herbicide. The homogeneous blend of the present invention also reduces the safety hazard arising from mixing. Because the blend of water, ammonium sulfate and alkyl polysaccharide may be pre-prepared in a single container, the applicator need only add the blend to a solution of glyphosate and water to make a solution that is effective and efficient in killing weeds. The empty container may be disposed or may be refilled.

It has surprisingly been found that the increased concentration of dissolved ammonium sulfate in the herbicidal blend is made possible because of the use of alkyl polysaccharide. The alkyl polysaccharide is sold under the name, Agrimule PG 2069 ®, APG 325 ®, manufactured by the Henkel Corporation of Ambler, Pa. The Agrimule PG 2069 ® includes alkyl polyglycoside polymers with alkyl chains of nine carbon atoms in a concentration of 20% by weight, ten carbon atoms in a concentration of 40% by weight and eleven carbon atoms in a concentration of 40% by weight. The alkyl polyglycoside has an average degree of polymerization of 1.6. The alkyl polyglycoside is a nonionic surfactant. The alkyl polyglycoside is non-gelling, biodegradable and soluble in dispersions of high salt concentrations.

One other alkyl polysaccharide supplier is ICI Surfactant of Wilmington, Del. The alkyl polysaccharide manufactured by ICI Surfactant has a trade name AT PLUS 452 ®. The alkyl polysaccharide is based on glucose and fatty alcohols derived from plant sources. Its presence in the herbicidal blend assures that the ammonium sulfate will remain dissolved in the blend even at high concentrations and even in the presence of glyphosate. That the alkyl polysaccharide effectively disperses ammonium sulfate and glyphosate to make a homogeneous herbicidal blend is surprising because other nonionic surfactants such as nonoxynol were not successful in making a homogeneous adjuvant blend with ammonium sulfate.

The homogeneous herbicidal blend of the present invention has been compared to mixtures including glyphosate in a series of tests against a variety of broadleaf plants. The results of the tests are described below. The examples are presented to illustrate a range of performance of the herbicidal blend of the present invention and not to limit the blend.

The tests showed that glyphosate formulations lacking a fertilizer did not perform as well as glyphosate formulations having a fertilizer. The tests also showed that glyphosate formulations having a fertilizer but lacking a surfactant did not perform as well as glyphosate formulations having a surfactant. The tests further showed that the glyphosate formulation of the present invention had a consistently good performance while other formulations using other nonionic surfactants did not demonstrate a consistently good performance. This is believed to result from an inadequate dispersibility on the part of the other surfactants.

The tests surprisingly showed that the premix of the present invention in combination with glyphosate produced a comparable or better broadleaf plant kill rate than other herbicidal mixtures having a nonionic surfactant and ammonium sulfate even though the surfactant concentration in the blend of the present invention was less than one-half the concentration of other surfactants. Further, the ammonium sulfate concentration was less for the blend of the present invention than for the other nonionic surfactant-glyphosate blends.

EXAMPLE 1

Testing was performed by the Crop and Weed Sciences Department of North Dakota State University in Fargo, N.D. In a first test, mixtures of ammonium sulfate, surfactants, and glyphosate were compared. The mixtures were compared when applied on broadleaf plants that included 'Grandin' hard red spring wheat, 'Linton' flax, and 'Sunup' proso millet (Prmi). These plants were seeded in adjacent strips as bioassay species on May 11, 1992. The herbicidal mixtures were applied to the plants when the plants had the following maturities: 12- to 14-inch tall flax, 5- to 6-leaf millet, and 3- to 8-inch tall broadleaf plants.

The mixtures were applied on Jun. 26, 1992, when ambient conditions included a temperature of 72° F., a 42% relative humidity, partly cloudy sky, and 8.5 mile per hour (mph) wind. The mixtures were applied with a bicycle wheel type plot sprayer delivering 8.5 gallons of each mixture per acre (gpa) at 35 psi through 8001 flat fan nozzles to a 7 ft. wide area on plots having dimensions of 10 ft. by 25 ft. The experiment was a randomized complete block design with four replicates. A summary of the data acquired by this test is described in Tables 1A and 1B.

TABLE 1-A

| Treatment | Rate oz/A | July 8 All Species % | Wheat % |
|---|---|---|---|
| Glyphosate + X-77 ® | 1.5 + 1% | 74  87 | 100 |
| Glyphosate + Cayuse ® + R-11 ® | 1.5 + 0.5% + 1% | 93  93 | 100 |
| Glyphosate + INV Premix | 1.5 + 2% | 93  96 | 100 |
| Glyphosate + SulfacDG ® + Spray Fuse 90 ® | 1.5 + pH5 + 1% | 8  35 | 64 |

TABLE 1-A-continued

| Treatment | Rate oz/A | July 8 All Species | Wheat |
|---|---|---|---|
| | | % | |
| Glyphosate + AMS + X-77 ® | $1.5 + \frac{11.6 \text{ lbs}}{100 \text{ gal}} + 1\%$ | 94   97 | 100 |
| Glyphosate | | — — | 72 |
| C.V. % | | 8   17 | 7 |
| LSD 5% | | 9   21 | 10 |
| # of REPS | | 4   4 | 4 |

TABLE 1-B

| Treatment | Rate oz/A | Flax | Prmi | Broadleaf weeds |
|---|---|---|---|---|
| | | % | | |
| Glyphosate + X-77 ® | 1.5 + 1% | 28 | 85 | 31 |
| Glyphosate + Cayuse ® + R-11 ® | 1.5 + 0.5% + 1% | 69 | 93 | 46 |
| Glyphosate + INV Premix | 1.5 + 2% | 65 | 98 | 42 |
| Glyphosate + SlufacDG ® Spray Fuse 90 ® | 1.5 + pH5 + 1% | 5 | 49 | 5 |
| Glyphosate + AMS + X-77 ® | $1.5 + \frac{11.6 \text{ lbs}}{100 \text{ gal}} + 1\%$ | 57 | 100 | 59 |
| Glyphosate | | 11 | 46 | 4 |
| C.V. % | | 25 | 17 | 54 |
| LSD 5% | | 17 | 20 | 28 |
| # of REPS | | 4 | 4 | 4 |

The glyphosate and X-77 ® blend described in Tables 1-A and 1-B refers to a blend of glyphosate and a nonionic surfactant. The nonionic surfactant, X-77 ®, is a mixture of alkylarylpolyoxyethylene, glycols, free fatty acids and isopropanol, manufactured by Valent U.S.A. Corp. of Walnut Creek, Calif.

The Cayuse ® ingredient includes a phosphate ester of polyglycoethers, ammoniated salts, and inert ingredients. The Cayuse ® ingredient is manufactured by the Wilber-Ellis Corporation of Friona, Tex. The R-11 ® surfactant includes octylphenoxypolyethoxy ethanol, isopropanol and compounded silica. The R-11 ® surfactant is manufactured by the Wilber-Ellis Corp. of Friona, Tex.

The Sulfac DG ®, a sulfonated surfactant, includes sodium bisulfate, in a concentration of 93.7% by weight and inert ingredients of 6.3% by weight. The Sulfac DG ® is manufactured by Cornbelt Chemical Company of McCook, Neb.

The Spray Fuse 90 ® surfactant includes alkylarylpolyoxyethylene, glycose, free fatty acids and isopropanol in a concentration of 90% by weight. The Spray Fuse 90 ® is manufactured by Cornbelt Chemical Company of McCook, Neb. The AMS in the tables refers to ammonium sulfate.

The rates of application for glyphosate and X-77 ® refers to 1.5 ounces of glyphosate in an aqueous mixture applied to each acre of broadleaf plants, the mixture having 1% of the X-77 ® surfactant by volume. The rate of application of the glyphosate, Cayuse ® and R-11 ® mixtures refers to an application of 1.5 ounces of glyphosate in an aqueous mixture per acre having a concentration of Cayuse ® of 0.5% by volume and a concentration of R-11 ® of 1% by volume. The rate of application of the SulfacDG ® was such that the SulfacDG ® was added to the mixture until the pH of the mixture reached 5. The mixture was applied so that 1.5 ounces of glyphosate was applied to each acre. The mixture included 1% by volume Spray Fuse 90 ®.

The rate of application for the glyphosate blend of the present invention refers to a rate of application of 1.5 ounces per acre of glyphosate where the premix of the present invention is 2% of the total volume applied. The premix included ammonium sulfate, alkyl polysaccharide and water. The rate of application of the premix was 0.17 gallons per acre based on a total application of 8.5 gallons per acre. The quantity, 0.17 gallons, is 2% of 8.7 gallons. Considering that the premix had 8.5 pounds of ammonium sulfate per 2.5 gallons, ammonium sulfate was applied at a rate of 0.58 pounds or 9.2 ounces per acre. The quantity of 0.58 pounds of ammonium sulfate per 0.17 gallons of premix is of the same ratio as 8.5 pounds of ammonium sulfate per 2.5 gallons of premix. Considering that the surfactant was added to the premix in a concentration of 0.034 gallons per 0.17 gallons of the premix or 8.5 gallons of the total volume applied, the surfactant was applied at a rate of 0.4% by volume per acre.

The mixture of the glyphosate, SulfacDG ®, and Spray Fuse 90 ® refers to a glyphosate application rate of 1.5 ounces per acre, the glyphosate aqueous mixture having 1% of SulfacDG ® and Spray Fuse 90 ®.

The rate for application of glyphosate, ammonium sulfate (AMS), and X-77 ® was 1.5 ounces per acre of the glyphosate aqueous mixture having 11.6 pounds ammonium sulfate per 100 gallons of the mixture. The X-77 ® surfactant was 1% by volume of the quantity of mixture applied per acre.

The least significant difference (LSD) for all species was 9% on May 11, 1992 and 21% on Jun. 26, 1992. The LSD for wheat was 10%, for flax, 11%, for proso millet, 20%, and for broadleaf weeds, 20% on June 26, 1992.

The data showed that control of most species by glyphosate was enhanced significantly more when accompanied by ammonium sulfate (AMS) as compared to glyphosate applied alone. However when a mixture of AMS and glyphosate further included Sulfac DG ® in conjunction with a Spray Fuse 90 ®, the performance of this mixture resulted in a kill of only 5% of flax, 49% of proso millet and 5% of broadleaf weeds.

This performance was worse than that of glyphosate alone.

The glyphosate provided 90% or more proso millet control when applied as a mixture of Cayuse®+R-11®, the premix of the present invention, designated INV premix, and ammonium sulfate (AMS)+X-77®. The R-11®, X-77® and alkyl polysaccharide of the present invention are nonionic surfactants. The comparable performance of the premix of the present invention was achieved even though the surfactant concentration was 0.4%, less than one-half the surfactant concentration of the other mixtures.

EXAMPLE 2

The plants of 'Stoa' hard red spring wheat, 'Neche' flax, 'Dumont' oats, and 'Common red' proso millet (Prmi) were seeded in adjacent strips as bioassay species on May 20, 1992. The herbicidal mixtures were applied to the plants when they reached a height of 6- to 9-inches tall on Jun. 25, 1992. The ambient temperature during application was 70° F. The sky was partly cloudy with 0- to 10-mph winds. The herbicidal mixtures were applied with a bicycle-wheel type plot sprayer delivering 8.5 gpa at 35 psi through 8001 flat fan nozzles to a 5 ft. wide area over plots with dimensions of 10 ft. by 25 ft. The experiment was a randomized block design with four replicates.

monium sulfate solution with the X-77® surfactant displayed a performance that was much more unpredictable than that of the blend of the present invention, INV premix. Even though the glyphosate-ammonium sulfate-X-77® solution included a much higher concentration of surfactant and ammonium sulfate than was used for the premix of the present invention, the results in Table 2 showed that this composition had a worse performance than that of the present invention. As discussed, the premix of the present invention was applied at a rate of 9.2 ounces of AMS per acre and a rate of alkyl polysaccharide of 0.4% by volume.

The superior performance of the present invention is believed to result from the improved handling performance of the herbicidal blend of the present invention as compared to a mixture of ammonium sulfate, glyphosate and just about any other surfactant. The improved handling performance results from the use the alkyl polysaccharide surfactant that reliably increases the dispersibility of ammonium sulfate when combined with glyphosate.

EXAMPLE 3

'Butte 86' hard red spring wheat, 'Hybrid Pearl' proso millet, a mixture of soybeans, sunflowers, oats, barley, and flax were seeded in adjacent strips May 26, 1992. The herbicidal mixtures were applied to 24-inch

TABLE 2-A

| Treatment | Rate oz/A | July 8 | | | |
|---|---|---|---|---|---|
| | | Wheat | Flax | Oats | Prmi |
| | | % | | | |
| Glyphosate + X-77® | 1 + 1% | 18 | 16 | 20 | 26 |
| Glyphosate + Cayuse® + R-11® | 1 + 0.5% + 1% | 50 | 55 | 43 | 35 |
| Glyphosate + INV Premix | 1 + 2% | 55 | 44 | 41 | 48 |
| Glyphosate + SulfacDG® + Spray fuse 90® | 1 + pH5 + 1% | 21 | 11 | 11 | 14 |
| Glyphosate + AMS + X-77® | 1 + $\frac{11.6 \text{ lbs}}{100 \text{ gal}}$ + 1% | 23 | 23 | 34 | 35 |
| Glyphosate | 1 + 0 | 6 | 6 | 8 | 4 |
| C.V. % | | 39 | 32 | 37 | 54 |
| LSD 5% | | 20 | 14 | 19 | 23 |
| # of REPS | | 4 | 4 | 4 | 4 |

TABLE 2-B

| Treatment | Rate oz/A | July 27 | | | |
|---|---|---|---|---|---|
| | | Wheat | Flax | Oats | Prmi |
| | | % | | | |
| Glyphosate + X-77® | 1 + 1% | 32 | 10 | 37 | 22 |
| Glyphosate + Cayuse® + R-11® | 1 + 0.5% + 1% | 62 | 52 | 67 | 54 |
| Glyphosate + INV Premix | 1 + 2% | 55 | 50 | 63 | 36 |
| Glyphosate + SulfacDG® + Spray fuse 90® | 1 + pH5 + 1% | 20 | 11 | 20 | 12 |
| Glyphosate + AMS + X-77® | 1 + $\frac{11.6 \text{ lbs}}{100 \text{ gal}}$ + 1% | 52 | 32 | 56 | 43 |
| Glyphosate | 1 + 0 | 18 | 9 | 18 | 10 |
| C.V. % | | 27 | 38 | 24 | 38 |
| LSD 5% | | 20 | 19 | 19 | 23 |
| # of REPS | | 4 | 4 | 4 | 4 |

The data showed that glyphosate control of most species studied was enhanced when the glyphosate was used in conjunction with ammonium sulfate as compared to glyphosate alone. Compositions including the surfactants of X-77®, Sulfac DG® and Spray Fuse 90® were also employed.

The percent of broadleaf plants killed was measured on two different dates, Jul. 8 and July 22. The data showed that the performance of glyphosate in an amtall wheat, 6-inch tall proso millet (Prmi), 4-inch tall soybeans (Sobe), 4-leaf sunflower (Sufl) and barley (Barl), 3.5-leaf oats, and 2-inch tall flax on Jul. 14, 1992. The ambient temperature for application was 84° F. with a clear sky, and a 10 mph wind. The herbicidal mixtures were applied with a bicycle wheel type plot sprayer delivering 8.5 gpa at 35 psi through flat fan-type nozzles. One replicate of each species was treated and evaluated.

TABLE 3-A

| Treatment | Rate oz/A | Wheat | Sufl | Prmi | Oat |
|---|---|---|---|---|---|
| | | | % | | |
| Glyphosate + X-77 ®(NIS) | 1 + 1% | — | 70 | 20 | 50 |
| Glyphosate + Cayuse + R-11 ® | 1 + 0.5% + 1% | 50 | 50 | — | 75 |
| Glyphosate and INV Premix | 1 + 2% | 75 | 90 | 80 | 85 |
| Glyphosate + SulfacDG ® + Spray fuse 90 ® | 1 + pH5 + 1% | 20 | 20 | 10 | 75 |
| Glyphosate + AMS + X-77 ® | $1 + \frac{11.6 \text{ lbs}}{100 \text{ gal}} + 1\%$ | 50 | 85 | 20 | 50 |
| Untreated | | 0 | 0 | 0 | 10 |

TABLE 3-B

| Treatment | Rate oz/A | Barl | Sobe | Flax |
|---|---|---|---|---|
| | | | % | |
| Glyphosate + X-77 ®(NIS) | 1 + 1% | 10 | 50 | 60 |
| Glyphosate + Cayusee ® + R-11 ® | 1 + 0.5% + 1% | 80 | 50 | 85 |
| Glyphosate + INV Premix | 1 + 2% | 80 | 90 | 90 |
| Glyphosate + SulfacDG ® + Spray fuse 90 ® | 1 + pH5 + 1% | 0 | — | 0 |
| Glyphosate + AMS + X-77 ® | $1 + \frac{11.6 \text{ lbs}}{100 \text{ gal}} + 1\%$ | 85 | 70 | 80 |
| Untreated | | 0 | — | 10 |

All glyphosate mixtures that included salt adjuvant fertilizers generally enhanced plant species control by glyphosate as compared to mixtures having only surfactants such as X-77 ® or Sulfac DG ® and Spray Fuse 90 ®. Glyphosate dispersed at 1 oz./acre applied without surfactant was not effective in controlling any of the plant species. With the exception of barley, the homogeneous herbicidal blend of the present invention (INV) performed much more effectively in killing weeds than did the mixture of glyphosate, ammonium sulfate, and X-77 ®.

EXAMPLE 4

'Siberian' foxtail millet (Sbmi), 'Excel' barley (Brly), and 'McCall' soybean (Sobe) were seeded in adjacent strips on Jun. 26, 1992. The herbicidal mixtures were applied to 6- to 6.5-leaf foxtail millet, 14- to 16-inch tall barley, and third trifoliolate soybeans on Aug. 6, 1992. The ambient temperature during application was 60° F., with a partly cloudy sky and fog, 0- to 8-mph wind, and wet conditions from heavy dew. The herbicidal mixtures were applied with a bicycle-wheel-type plot sprayer delivering 8.5 gpa at 35 psi through flat fan nozzles to a 7 ft. wide area having a length of 10 by 25 ft. plots. The experiment was randomized complete block design with four replicates.

TABLE 4-A

| Treatment | Rate oz/A | August 17 | | |
|---|---|---|---|---|
| | | Sbmi | Brly | Sobe |
| Glyphosate + X-77 ®(NIS) | 1.5 + 1% | 97 | 83 | 61 |
| Glyphosate + Cayuse ® + R-11 ® | 1.5 + 0.5% + 1% | 99 | 97 | 65 |
| Glyphosate + INV Premix | 1.5 + 2% | 99 | 98 | 79 |
| Glyphosate + SulfacDG ® + Spray fuse 90 ® | 1.5 + pH5 + 1% | 92 | 61 | 50 |
| Glyphosate + AMS + X-77 ® | $1.5 + \frac{11.6 \text{ lbs}}{100 \text{ gal}} + 1\%$ | 98 | 97 | 81 |
| Untreated | | 0 | 0 | 0 |
| C.V. % | | 5 | 11 | 19 |
| LSD 5% | | 7 | 14 | 17 |
| # OF REPS | | 4 | 4 | 4 |

TABLE 4-B

| Treatment | Rate oz/A | August 27 | | |
|---|---|---|---|---|
| | | Fxtl | Brly | Sobe |
| | | | % | |
| Glyphosate + X-77 ®(NIS) | 1.5 + 1% | 70 | 86 | 30 |
| Glyphosate + Cayusee + R-11 ® | 1.5 + 0.5% + 1% | 89 | 97 | 38 |
| Glyphosate + INV | 1.5 + 2% | 94 | 99 | 64 |
| Glyphosate + Sulfac DG ® + Spray fuse 90 ® | 1.5 + pH5 + 1% | 73 | 79 | 23 |
| Glyphosate + AMS + X-77 ® | $1.5 + \frac{11.6 \text{ lbs}}{100 \text{ gal}} + 1\%$ | 89 | 98 | 64 |

TABLE 4-B-continued

| Treatment | Rate oz/A | August 27 | | |
|---|---|---|---|---|
| | | Fxtl | Brly | Sobe |
| | | % | | |
| Untreated | | 0 | 0 | 0 |
| C.V. % | | 12 | 5 | 36 |
| LSD 5% | | 14 | 7 | 22 |
| # OF REPS | | 4 | 4 | 4 |

As Table 4-B shows, all glyphosate mixtures having salt adjuvant fertilizers enhanced grass species control by glyphosate as compared to herbicidal mixtures applied with X-77 ®, except for Sulfac DG ® and Spray Fuse 90 ®. However, control of soybeans was only enhanced by the herbicidal blend of the present invention which included, INV premix, and ammonium sulfate (AMS).

EXAMPLE 5

Testing was performed at the University of Wisconsin at River Falls, Wis. Oats, C. ragweed, C. lambsquarter, P. smartweed, B. nightshade, G. foxtail, and W. buckwheat were seeded in adjacent strips as bioassay species. When the oats reached a height of 6 to 10 inches tall, having five leaf jointing, and other weeds reached a height of 1 to 5 inches tall, herbicidal mixtures were applied to each of four replicate plots per herbicidal mixture. The herbicidal mixtures were applied the morning of Jun. 8, 1993. The application preceded a rain at about 1:00 p.m. A drift control agent was applied in conjunction with a herbicidal mixture at a concentration of 2 ounces per 100 gallons. The rate of application of the glyphosate was 10 ounces per acre. The Preference ® adjuvant refers to a mixture of nonoxynol in a concentration of about 38% to about 80% by volume, acidulated soybean soapstock in a concentration of 10 to 30% by volume, about 5 to 10% for viscosity reducing agent such as isopropanol or n-butynol and about 5 to 10% water. The Preference ® may also acceptably include fatty acid ethoxylate and antifoam in a range of 10 to 20% by volume and 0.2 to 0.5% by volume, respectively. The results show a very good kill rate for the glyphosate in combination with the adjuvant blend of the present invention.

TABLE 5-A

1993 GLYPHOSATE SURFACTANT STUDY
UNIVERSITY OF WISCONSIN-RIVER FALLS

| Teatment | Rate | Rep | | | | Mean |
|---|---|---|---|---|---|---|
| | | I | II | III | IV | |
| Glyphosate INV | 10.0 ozs/acre 5% | 95 | 98 | 98 | 95 | 97 |
| Glyphosate Preference ® | 10.0 ozs/acre .5% | 80 | 65 | 50 | 45 | 60 |
| Glyphosate X-77 | 10.0 ozs/acre .5% | 35 | 35 | 50 | 35 | 39 |
| Glyphosate Preference ® Ammonium Sulfate | 10.0 ozs/acre .5% 8.5 lbs/100 gals | 90 | 95 | 85 | 90 | 90 |
| Glyphosate X-77 Ammonium Sulfate | 10.0 ozs/acre .5% 8.5 lbs/100 gals | 85 | 90 | 85 | 95 | 89 |

Although the present invention has been described with reference to preferred embodiments, workers skilled in the art will recognize that changes may be made in form and detail without departing from the spirit and scope of the invention.

What is claimed is:

1. (Amended) A homogeneous blend for use with glyphosate, the blend comprising water, ammonium sulfate and alkyl polysaccharide, with a concentration of about 8.5 pounds of ammonium sulfate for about 2.5 gallons of the blend.

2. A method for killing broadleaf weeds comprising:
   making a premix comprising ammonium sulfate, alkyl polysaccharide and water wherein the ammonium sulfate has a concentration of about 8.5 pounds for about 2.5 gallons of the premix;
   adding the premix to an aqueous glyphosate mixture to make a homogeneous glyphosate blend; and
   applying the homogeneous glyphosate blend to broadleaf weeds.

* * * * *

UNITED STATES PATENT AND TRADEMARK OFFICE
CERTIFICATE OF CORRECTION

PATENT NO. : 5,356,861

DATED : October 18, 1994

INVENTOR(S) : JOE V. GEDNALSKE, ROBERT W. HERZFELD

It is certified that error appears in the above-indentified patent and that said Letters Patent is hereby corrected as shown below:

On the Title Page, item [54] and column 1, line 2, delete "HOMOGENOUS", insert --HOMOGENEOUS--.

On the Title Page, under item [19] and item [75], delete "Gednalski", insert --Gednalske--.

On the Title Page of the Patent, at line 3 of OTHER PUBLICATIONS, delete "Hoorne et al. "Novel Adjusvants for Agrodremical for Medetions Based on Sugar Ethers", ICI Reprint RP67/91e. 1991."

insert --Hoorne et al. "Novel Adjuvants for Agrochemical Formulations Based on Sugar Ethers", ICI Reprint RP67/91e. 1991.--

Col. 1, line 8, delete "homogenous", insert -- homogeneous--

Col. 1, line 12, delete "homogenous", insert --homogeneous--

Col. 2, line 10, delete "nonionic", insert --non-ionic--

Col. 3, line 46, delete "nonionic", insert --non-ionic--

Col. 4, line 2, delete "nonionic", insert --non-inonic--

Col. 4, line 20, delete "nonionic", insert --non-inonic--

Col. 4, line 27, delete "nonionic", insert --non-inonic--

Col. 4, line 33, delete "nonionic", insert --non-inonic--

Col. 5, in TABLE 1-B, delete "SlufacDG® Spray Fuse 90®", insert -- SulfacDG® + Spray Fuse 90®--

UNITED STATES PATENT AND TRADEMARK OFFICE
CERTIFICATE OF CORRECTION

PATENT NO. : 5,356,861

DATED : October 18, 1994

INVENTOR(S) : JOE V. GEDNALSKE, ROBERT W. HERZFELD

It is certified that error appears in the above-indentified patent and that said Letters Patent is hereby corrected as shown below:

Col. 5, line 30, delete "nonionic" (both occurrences), insert --non-ionic--

Col. 7, line 8, delete "nonionic", insert --non-ionic--

Cols. 9-10, in TABLE 3-A, delete "Cayuse", insert --Cayuse®--

Cols. 9-10, in TABLE 3-B, delete "Cayusee", insert --Cayuse--

Cols. 9-10, in TABLE 4-B, delete "Cayusee", insert --Cayuse®--

Cols. 9-10, in TABLE 4-B, delete "INV", insert -- INV Premix--

Signed and Sealed this

Twenty-eight Day of February, 1995

Attest:

BRUCE LEHMAN

*Attesting Officer*     *Commissioner of Patents and Trademarks*